United States Patent

Sato et al.

[11] Patent Number: 5,449,815
[45] Date of Patent: Sep. 12, 1995

[54] PROSTAGLANDIN $E_1$ ANALOGUES

[75] Inventors: Fumie Sato, 1-219, Kugenumahigashi 3-Chome, Fujisawa, Kanagawa 251; Takehiro Amano, Urawa; Kazuya Kameo, Kounosu; Tohru Tanami, Tokyo; Masaru Mutoh, Ohmiya; Naoya Ono, Tokyo; Jun Goto, Ohmiya, all of Japan

[73] Assignees: Taisho Pharmaceutical Co., Ltd.; Fumie Sato, both of Japan

[21] Appl. No.: 137,090

[22] PCT Filed: Apr. 21, 1992

[86] PCT No.: PCT/JP92/0514

§ 371 Date: Oct. 19, 1993

§ 102(e) Date: Oct. 19, 1993

[87] PCT Pub. No.: WO92/18473

PCT Pub. Date: Oct. 29, 1992

[30] Foreign Application Priority Data

Apr. 22, 1991 [JP] Japan .................................. 3-182112
Aug. 27, 1991 [JP] Japan .................................. 3-296739

[51] Int. Cl.$^6$ ............................................. C07C 405/00
[52] U.S. Cl. .................................... 560/121; 556/441; 562/503
[58] Field of Search ...................... 560/121; 502/503

[56] References Cited

FOREIGN PATENT DOCUMENTS 9316041 8/1993 WIPO .

*Primary Examiner*—Robert Gerstl
*Attorney, Agent, or Firm*—Lorusso & Loud

[57] ABSTRACT

Object: To provide novel prostaglandin $E_1$ analogues which have more excellent pharmaceutical effects, longer duration of the effects and less side-effects than the prior art prostaglandin $E_1$'s.

Constitution: A $PGE_1$ analogue represented by the formula:

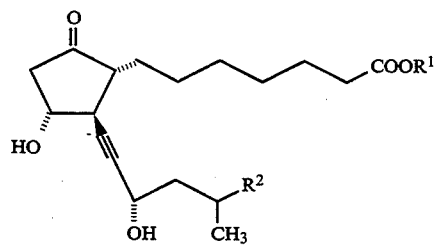

(wherein $R^1$ is a hydrogen atom, an alkyl group having 1 to 6 carbon atoms or an allyl group, and $R^2$ is an alkyl group having 3 to 6 carbon atoms, an alkenyl group having 3 to 6 carbon atoms), or a salt thereof.

9 Claims, No Drawings

PROSTAGLANDIN $E_1$ ANALOGUES

This application is a 371 of PCT/JP92/00514 filed Apr. 21, 1992.

TECHNICAL FIELD

The present invention relates to novel prostaglandin (hereinafter referred to as PG) $E_1$ analogues.

BACKGROUND ART

Since PG's exhibit various important biological effects in a trace amount, investigations have been made of the synthesis and biological activity of natural PG's and a large number of PG analogues with the intention of use as medicines.

Especially, $PGE_1$ is now commercially available as a drug for the improvement of peripheral circulatory disturbances because of having characteristic effects such as blood platelet aggregation inhibiting effect and blood pressure reducing effect, and therefore, a large number of $PGE_1$ analogues have also been studied. However, the prior art $PGE_1$ analogues are quickly metabolized in vivo and thereby have drawbacks such as lack of duration of the effect. Furthermore, the prior art $PGE_1$ analogues cannot be administered orally in a sufficiently high amount to obtain the satisfactory effects because of causing diarrhea as a side-effect.

On the other hand, the known 13, 14-didehydro $PGE_1$ analogues in which the double bond between the 13- and 14-positions of $PGE_1$ is replaced by a triple bond include 13,14-didehydro $PGE_1$ methyl ester and 6-hydroxy-13,14-didehydro $PGE_1$.

An object of the present invention is to provide novel $PGE_1$ analogues which have more excellent pharmaceutical effects, longer duration of the effect and less side-effects than the prior art $PGE_1$ analogues.

DISCLOSURE OF THE INVENTION

As a result of continued extensive research, the present inventors have found that the specific compounds having a triple bond between the 13- and 14-positions of the $PGE_1$ analogues, and a methyl group at the 17-position can solve the above-mentioned problems, and have accomplished the present invention.

The present invention is directed to a $PGE_1$ analogue represented by the formula:

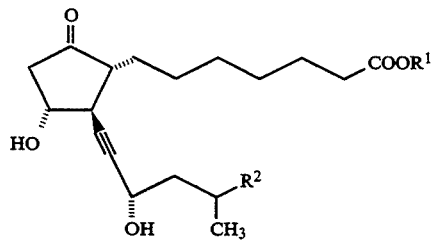

(wherein $R^1$ is a hydrogen atom, an alkyl group having 1 to 6 carbon atoms or an allyl group, and $R^2$ is an alkyl group having 3 to 6 carbon atoms or an alkenyl group having 3 to 6 carbon atoms), or a salt thereof.

In the present invention, the alkyl group having 1 to 6 carbon atoms refers to a straight or branched chain alkyl group (e.g. a methyl group, an ethyl group, an n-propyl group, an isopropyl group, an n-butyl group, an isobutyl group, a t-butyl group, an n-pentyl group and an isopentyl group). The alkyl group having 3 to 6 carbon atoms and the alkenyl group having 3 to 6 carbon atoms refer to a straight or branched chain alkyl group.

The salt of the compound of Formula (I) refers to salts thereof when $R^1$ is a hydrogen atom, for example, salts with metals (e.g. sodium, potassium and aluminium), or salts with organic amines (e.g. trialkylamine).

The compounds of Formula (I) can be prepared easily, for example, by the following processes:

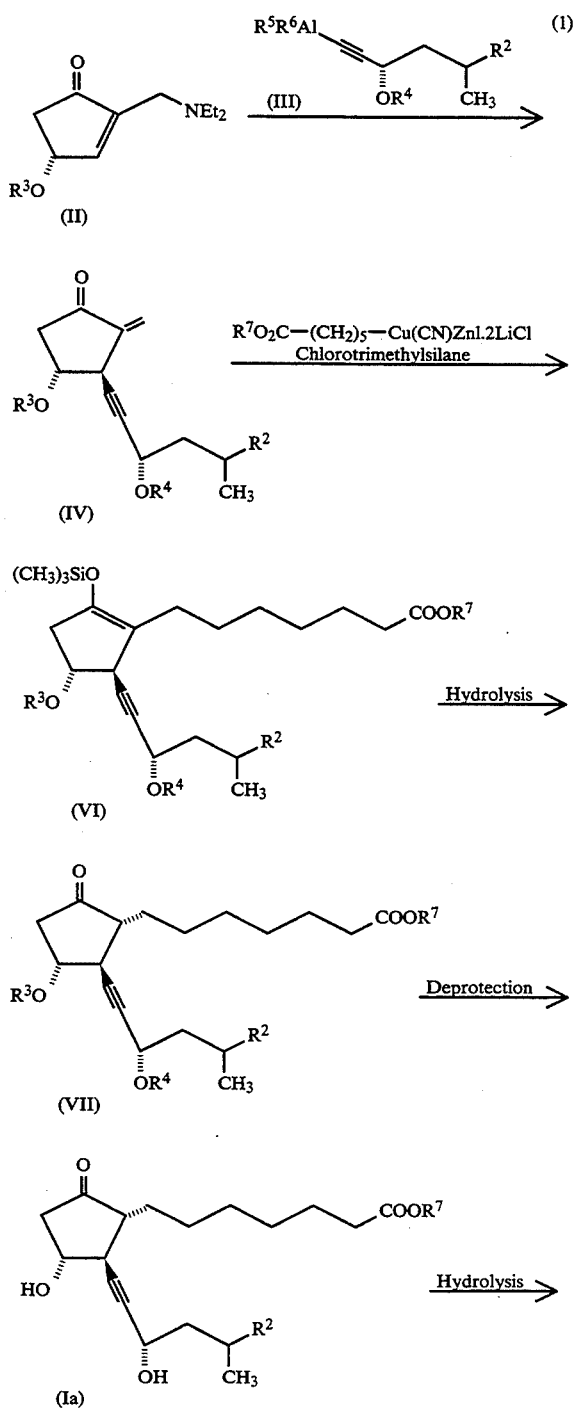

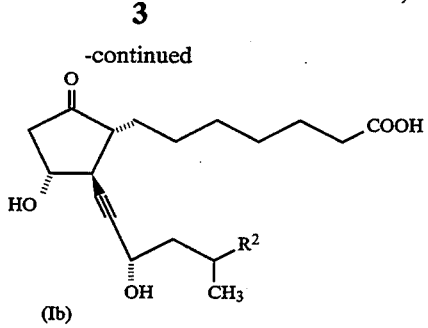

(wherein, $R^3$ and $R^4$ are the same or different, and are each a hydroxyl protecting group, $R^5$ and $R^6$ are the same or different, and are each an alkyl group having 1 to 10 carbon atoms, $R^7$ is the same as $R^1$, except a hydrogen atom, and $R^2$ is as defined above. The hydroxyl protecting group refers to those usually used in the field of prostaglandins, such as a t-butyldimethylsilyl group, a triethylsilyl group, a phenyldimethylsilyl group, a tetrahydropyranyl group, a tetrahydrofuranyl group, a methoxymethyl group, an ethoxyethyl group and a benzyl group).

① First, the known compound of Formula (II) is reacted with 0.8 to 2.0 equivalents of an organic aluminium compound of Formula (III) in an inert solvent (e.g. benzene, toluene, tetrahydrofuran, diethyl ether, methylene chloride or n-hexane) at a temperature of −10 to 30° C., preferably 0° to 10° C., according to the method of Sato et al. [Journal of Organic Chemistry, vol. 53, page 5590 (1988)] to give a compound of Formula (IV) stereo-specifically.

The organic aluminium compound of Formula (III) can be prepared, for example, by completely achieving the reaction of an acetylene compound represented by the formula

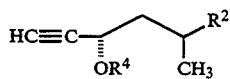

(wherein $R^2$ and $R^4$ are as defined above), which can be prepared according to the method of Sato et al. [Tetrahedron Letters, vol. 30, page 7083 (1989)], with 0.8 to 1.5 equivalents of an alkyllithium (e.g. n-butyllithium or t-butyllithium) at −20° to 30° C., preferably −10° to 0° C., more preferably 10° to 30° C., and then adding 0.8 to 1.5 equivalents of a halogenated alkylaluminium (e.g. diethylaluminium chloride or dimethylaluminium chloride) represented by the formula $$R^5R^6-Al-X$$

(wherein $R^5$ and $R^6$ are as defined above, and X is a halogen atom) at −20° to 30° C. In the reaction, it is preferable to use an inert solvent (e.g. benzene, toluene, tetrahydrofuran, diethyl ether, methylene chloride or n-hexane).

② Then, the compound of Formula (IV) is reacted with 0.5 to 4 equivalents of an organic copper compound of Formula (V) and 0.5 to 4 equivalents of chlorotrimethylsilane in an inert solvent (e.g. tetrahydrofuran, diethyl ether, methylene chloride, toluene or n-hexane) at −78° to 40° C. to give a compound of Formula (VI).

The organic copper compound of Formula (V) can be prepared from an iodide compound represented by the formula $$I-(CH_2)_5-COOR^7 \quad (VIII)$$

(wherein $R^7$ is as defined above) according to the known method [P. Knochel et al, Journal of Organic Chemistry, vol. 53, page 2390 (1988)]. That is, an iodide compound of Formula (VIII) is reacted with 0.8 to 5 equivalents of zinc activated, for example, by 1,2-dibromomethane, chlorotrimethylsilane and iodine in an inert solvent (e.g. tetrahydrofuran, diethyl ether, n-hexane, n-pentane or dioxane) to lead to an organic zinc compound represented by the formula:

$$IZn-(CH_2)_5-COOR^7$$

(wherein $R^7$ is as defined above). In this case, the reaction, if desired, may be carried out with heating. The heating temperature, while dependant on the boiling point of the solvent to be used, is usually 30° to 150° C., preferably 40° to 80° C. The resulting organic zinc compound is reacted at −50° to 10° C. with copper cyanide (1 to 2.5 equivalents) in the same inert solvent as described above including lithium chloride (2 to 5 equivalents) to give an organic copper compound of Formula (V).

③ The compound of Formula (VI) is hydrolyzed by using an inorganic acid (e.g. an aqueous hydrochloric acid solution) or an organic acid (e.g. p-toluenesulfonic acid) or an amine salt thereof (e.g. pyridinium p-toluenesulfonate) in an organic solvent (e.g. acetone, methanol, ethanol, isopropanol, diethyl ether or a mixture thereof) at 0° to 40° C. to stereoselectively give a compound of Formula (VII).

④ Finally, the hydroxyl protecting group of the compound of Formula (VII) is deprotected according to an ordinary method in the field of prostaglandins to give a compound of the present invention of Formula (I) wherein $R^1$ is other than a hydrogen atom [the compound of Formula (Ia)].

⑤ The compound of the present invention of Formula (I) wherein $R^1$ is a hydrogen atom [the compound of Formula (Ib)] can be prepared by hydrolyzing the ester moiety of the compound of Formula (Ia) wherein $R^7$ is an alkyl group having 1 to 6 carbon atoms [hereinafter referred to as compound of Formula (Ic)].

The hydrolysis is carried out by reacting the compound of Formula (Ic) with an enzyme in a buffer solution such as phosphate buffer or tris-hydrochloride buffer, if desired, by using an organic solvent (e.g. a water-miscible solvent such as acetone, methanol or ethanol).

Examples of the enzyme to be used are enzymes produced by microorganisms (e.g. enzymes produced by microorganisms belonging to Candida sp. and Pseudomonas sp.), and enzymes prepared from animal organs (e.g. pig liver and pig pancreas). Examples of the commercially available enzyme are lipase VII (produced by Sigma Co.; derived from microorganism of Candida sp.), lipase AY (produced by Amano Pharmaceutical Co.; derived from microorganism of Candida sp.), lipase MF (produced by Amano Pharmaceutical Co.; derived from microorganism of Pseudomonas sp.), PLE-A (produced by Amano Pharmaceutical Co.; prepared from pig liver), esterase (produced by Sigma Co.; prepared from pig liver), liphase II (produced by Sigma Co.;

prepared from pig pancreas) and lipoprotein lipase (produced by Tokyo Kasei Kogyo Co.; prepared from pig pancreas).

The amount of the enzyme to be used, while dependant on tile potency of the enzyme and the amount of the substrate [the compound of Formula (Ic)], is usually 0.1 to 20 times (by weight) relative to the substrate.

The reaction temperature is from 25° to 50° C., preferably 30° to 35° C.

(2) The compound of the present invention of Formula (I) wherein $R^1$ is a hydrogen atom can be also prepared from the compound of Formula (VII) wherein $R^7$ is an allyl group in the above item (1) according to the following process.

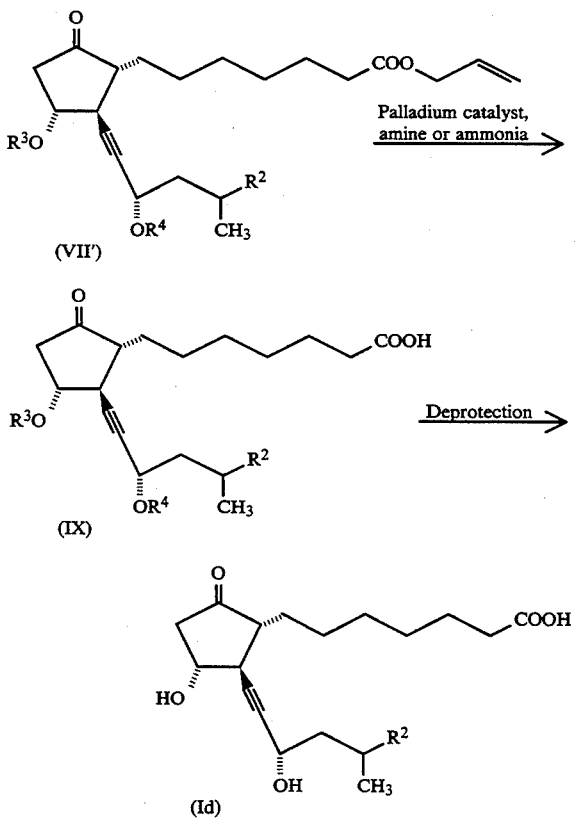

(wherein, $R^2$, $R^3$ and $R^4$ are as defined above).

① The compound of Formula (VII) wherein $R^7$ is an allyl group [the compound of Formula (VII')], in the above item (1) is first reacted with 1 to 10 equivalents of an organic amine or ammonia in the presence of a palladium catalyst to give a compound of Formula (IX).

Examples of the palladium catalyst are tris(dibenzylideneacetone)dipalladium(0)chloroform, bis(dibenzylideneacetone)palladium(0), tetrakis-(triphenylphosphine)palladium(0), bis(acetylacetonate)-palladium(II) and dichlorobis(benzonitrile)palladium (II). The amount of the palladium catalyst to be used is from 0.01 to 0.5 equivalent.

Examples of the organic amine are a primary or secondary organic amine such as, for example, ethylamine, diethylamine, morpholine and piperidine.

The reaction may be carried out, if necessary, in an inert organic solvent (e.g. diethyl ether or tetrahydrofuran). Also, it is preferable to add a phosphine (e.g. triethylphosphine, tributylphosphine or triphenylphosphine), unless phosphine forms a coordination compound with palladium as a catalyst.

② The hydroxyl protecting group of the compound of Formula (IX) is deprotected according to an ordinary method in the field of prostaglandins to give the compound of the present invention of Formula (I) wherein $R^1$ is a hydrogen atom [i.e. the compound of Formula (Id)].

The compounds of the present invention can be administered orally or parenterally (e.g. intravenously, rectally or vaginally) in a dosage form such as solid forms (e.g. tablets, granules or capsules) and liquid forms (e.g. solutions, fat emulsions or liposome suspensions). For use of the oral dosage forms, the compounds of the present invention can be formulated into the form of the inclusion compounds with $\alpha$-, $\beta$- or $\gamma$-cyclodextrin, or methylated cyclodextrin. Examples of the intravenous dosage forms are aqueous or non-aqueous solutions, emulsifiers, suspensions and solid formulations capable of dissolving in a solvent for injection immediately before use.

The rectal dosage forms include suppositories, and vaginal dosage forms include pessaries. The dose is from 0.1 to 100 μg, given in a single dose or up to 3 divided doses a day.

INDUSTRIAL UTILIZATION

It is apparent from the experiments described below that the compounds of the present invention have a potent blood platelet aggregation inhibiting effect and a long duration of such effect. Furthermore, the compounds of the present invention are useful as therapeutical drugs of various diseases including peripheral circulatory disturbances because they rarely induce diarrhea which is the largest problem caused by a dose of PG's exhibiting positive pharmaceutical effect.

The effects of the present invention are illustrated in more detail by the following experiments. Experiment 1 [Guinea-pig blood platelet aggregation inhibition test]

Groups of five or six male Hartley strain guinea-pigs, each weighing 300 to 500 g, were used for the test after an overnight fast. A solution of the test drug in ethanol was suspended in 0.5% carboxymethyl-cellulose solution to give a final ethanol concentration of 1% or below. The test drug was orally administered in the amount of 50 μg/kg (5 cc of the solution per kg). Two or four hours later, animals were anesthetized by abdominal administration of 20 mg/kg of pentobarbital. After laparotomy, blood was collected from the abdominal artery using a plastic syringe, and mixed with 3.2% sodium citrate in a volume ratio of 9:1. The blood was centrifuged at 120×g for 10 minutes to give PRP as a supernatant. The remaining blood was further centrifuged at 1100×g for 10 minutes to give platelet poor plasma (PPP). The platelet count of PRP was adjusted to 4–6×$10^5$/mm$^3$ by using PPP. Blood platelet aggregation was determined according to the method of Born [Nature, vol. 194, page 927 (1962)]. That is, 275 μl of PRP was incubated with stirring at 1000 rpm at 37° C. for 3 minutes by using an aggrigometer, and then 25 μl of ADP (final concentration: 3 μM) or 25 μl of collagen (final concentration: 3 μg/ml) was added in order to induce blood platelet aggregation, and the maximum change of the light transmission obtained within 5 minutes was expressed as the maximum aggregation rate. From the following formula was calculated the aggregation inhibition rate of the group treated with the test drug to the maximum inhibition rate of the group treated with 0.5% carboxymethylcellulose solution as a control group.

$$\text{Aggregation inhibition rate (\%)} = \left(1 - \frac{\text{Maximum aggregation rate of group treated with test drug}}{\text{Maximum aggregation rate of control group}}\right) \times 100$$

Results are shown in Table 1. In the table are recited data of the compound obtained by converting the triple bond between the 13- and 14-positions and between the 2- and 3-positions of Compound 1 of Example 1 into double bonds as a comparative compound (limaprost) [Tsuboi et al, Arch. Intern. Pharmacodyn. Ther., vol. 247, page 89 (1980)].

In the experiment, the state of stool was observed for 2 hours after administration. As a result, significant diarrhea was found in the group treated with limaprost, and soft stool only was found in the group treated with the compounds of the present invention.

TABLE 1

| | Aggregation Inhibition Rate (%) | | | |
|---|---|---|---|---|
| | 2 hours after administration | | 4 hours after administration | |
| Test drug | ADP Aggregation | Collagen Aggregation | ADP Aggregation | Collagen Aggregation |
| Compound 2 | 23.4 | 18.7 | | |
| Compound 3 | 37.8 | 83.7 | | |
| Compound 5 | 65.8 | 100.0 | 28.5 | 43.2 |
| limaprost | 3.4 | 16.2 | | |

$p < 0.05$

Experiment 2 [Rabbit blood platelet aggregation inhibition test]

Groups of four New Zealand white strain rabbits, each weighing 2.5 to 4.0 kg, were used for the test. Blood was collected from the general carotid artery of the rabbits under an ether anesthesia, and mixed with 3.2% sodium citrate in a volume ratio of 9:1. The collected blood was centrifuged at 1100 rpm for 15 minutes to give platelet rich plasma (PRP) as a supernatant% Blood platelet aggregation was determined according to the method of Born [Nature, vol. 194, page 927 (1962)]. That is, 1 $\mu$l of the test drug dissolved in ethanol at the desired concentration was added to 275 $\mu$l of PRP, and the mixture was stirred at 1000 rpm at 37° C. Three minutes later, 25 $\mu$l of an aggregation-inducing agent [adenosine diphosphate (ADP), final concentration: 5 $\mu$M] was added thereto, and the maximum aggregation rate (which is the maximum change of the light transmission obtained within 5 minutes) was determined by using an aggregometer.

The aggregation inhibition rate was calculated on the basis of the aggregation obtained by using ethanol in place of the test drug solution, and the aggregation inhibition activity was expressed as $IC_{50}$ value which was determined from the dose response curve.

Results are shown in Table 2 wherein the compound number is as defined in the examples described hereinafter, and the $IC_{50}$ value is expressed as the mean value.

TABLE 2

| Test drug | $IC_{50}$ value (nM) |
|---|---|
| Compound 1 | 3.3 |
| Compound 2 | 1.4 |

TABLE 2-continued

| Test drug | $IC_{50}$ value (nM) |
|---|---|
| Compound 3 | 6.4 |
| Compound 4 | 2.8 |
| Compound 5 | 1.9 |
| limaprost | 6.3 |
| $PGE_1$ | 26 |

BEST MODE OF CARRYING OUT THE INVENTION

The present invention is illustrated in more detail by the following examples.

EXAMPLE 1

17S-17,20-Dimethyl-13,14-didehydro-$PGE_1$ methyl ester (Compound 1)

(1) (3S,5S)-3-(t-Butyldimethylsiloxy)-5-methylnona-1-ine (3.85 g) was dissolved in 28.8 ml of benzene, and then n-butyl lithium (1.95M, hexane solution, 6.4 ml) was added thereto at 0° C., followed by stirring for 30 minutes at the same temperature. Diethylaluminium chloride (0.97M, hexane solution, 14.8 ml) was added at 0° C. to the solution, the temperature of which was allowed to rise to room temperature, followed by stirring for 30 minutes.

(4R)-2-(N,N-Diethylamino)methyl-4-(t-butyldimethylsiloxy)cyclopent-2-en-1-one (0.25M, benzene solution, 38.4 ml) was added at room temperature to the solution, followed by stirring for 15 minutes.

The reaction solution was poured into a mixture of hexane (100 ml), a saturated aqueous ammonium chloride solution (100 ml) and an aqueous hydrochloric acid solution (3M, 30 ml) with stirring, and the organic layer was collected and washed with a saturated aqueous sodium bicarbonate solution (50 ml). The resulting organic layer was dried and concentrated to give a residue, which was then purified by silica gel column chromatography (eluent; hexane: ether=10:1) to give 3.72 g of (3R,4R)-2-methylene-3-[(3'S,5'S)-3'-(t-butyldimethylsiloxy)-5'-methylnon-1'-ynyl]-4-(t-butyldimethylsiloxy)cyclopentan-1-one.

$^1$H-NMR (CDCl$_3$, 200MHz) $\delta$ ppm:
0.09, 0.10 and 0.12(3s, 12H), 0.89(s, 18H), 0.80~0.99(m, 6H), 1.00~1.72(m, 9H), 2.32(dd, J=7.4Hz, 18.0Hz, 1H), 2.71(dd, J=6.6Hz, 18.0Hz, 1H), 3.47~3.56(m, 1H), 4.15~4.33(m, 1H), 4.44(dt, J=1.6Hz, 7.0Hz, 1H), 5.54(d, J=2.6Hz, 1H), 6.13(d, J=3.0Hz, 1H)

IR(neat):
2930, 2850, 1740, 1640, 1460, 1360, 1250, 1120, 1080, 835, 770cm$^{-1}$ (2) To 5-carbomethoxypentylzinc (II) iodide (0.86M tetrahydrofuran solution, 6.70 ml, 5.76 mmol) was added at −70° C., a solution of copper (I) cyanide.dilithium dichloride (1.26 g, 7.20 mmol) in 7.20 ml of tetrahydrofuran, followed by stirring at the same temperature for 15 minutes. To the solution was added at −70° C. a solution of the compound (1.42 g, 2.88 mmol) obtained in the above item (1) and trimethylsilyl chloride (0.658 ml, 5.18 mmol) in 10 ml of diethyl ether, followed by stirring to raise the temperature to room temperature over a period of about 2 hours.

The reaction solution, after addition of 43 ml of a saturated aqueous ammonium chloride solution, was extracted with n-hexane. The organic layer was washed with a saturated aqueous sodium chloride solution, dried and concentrated to give a residue, which was then dissolved in 14.4 ml of ether—isopropyl alcohol (1:4). To the solution was added pyridinium p-toluenesulfonate (36.2 mg, 0.144 mmol), followed by stirring at room temperature for 12 hours.

To the reaction solution were added 50 ml of ether and 10 ml of a saturated aqueous sodium bicarbonate solution, followed by extraction. The organic layer was dried and concentrated to give a residue, which was then chromatographed on silica gel column (eluent; n-hexane: ether=4:1) to give 1.19 g of (17S)-17,20-dimethyl-13,14-didehydro-PGE$_1$ methyl ester 11,15-bis(t-butyldimethylsilyl ether).

$^1$H-NMR (CDCl$_3$, 200MHz) δ ppm:
0.09(s, 3H), 0.10(s, 3H), 0.11(s, 3H), 0.13(s, 3H), 0.82~1.00(m, 6H), 0.89(s, 9H), 0.90(s, 9H), 1.06~1.83(m, 19H), 2.14~2.35(m, 1H), 2.17(dd, J=6.9Hz, 18.1Hz, 1H), 2.30(t, J=7.5Hz, 2H), 2.59~2.75(m, 1H), 2.67(ddd, J=1.4Hz, 6.6Hz, 18.1Hz, 1H), 3.66(s, 3H), 4.22~4.34(m, 1H), 4.42(dt, J=1.5Hz, 6.9Hz, 1H)

IR(neat):
2954, 2930, 2858, 2234, 1747, 1463, 1362, 1253, 1094, 838, 778cm$^{-1}$ (3) The compound (536 mg, 0.861 mmol) obtained in the above item (2) was dissolved in acetonitrile (29 ml), and then 50% aqueous hydrofluoric acid solution (6.9 ml) was added thereto at 0° C., followed by stirring at 0° C. for 90 minutes. The reaction solution was poured into ethyl acetate (40 ml) and a saturated aqueous sodium bicarbonate solution (245 ml). The mixture was extracted with ethyl acetate, washed with a saturated aqueous sodium bicarbonate solution and a saturated aqueous sodium chloride solution, dried and concentrated. The resulting residue was purified by silica gel column chromatography (eluent; ethyl acetate: methanol=40:1) to give 320 mg of the title compound.

$^1$H-NMR (CDCl$_3$, 300MHz) δ ppm:
0.82~0.96(m, 6H), 1.07~1.85(m, 19H), 2.16~2.33(m, 2H), 2.29(t, J=7.4Hz, 2H), 2.62(ddd, J=1.8Hz, 8.4Hz, 11.3Hz, 1H), 2.73(ddd, J=1.1Hz, 7.2Hz, 18.4Hz, 1H), 3.65(s, 3H), 4.25~4.35(m, 1H), 4.46(dt, J=1.5Hz, 7.1Hz, 1H)

IR(neat):
3400, 2920, 2230, 1730, 1440, 1160cm$^{-1}$

EXAMPLE 2

17RS)-20-Nor-17-methyl-19-(2'-methylprop-1'-enyl)-13,14-didehydro-PGE$_1$ methyl ester (1) Following a substantially similar manner to that of Example 1(1) but using (3S,5RS)-3-(t-butyldimethylsiloxy)-5,9-dimethyldec-8-en-1-yne in place of (3S,5S)-3-(t-butyldimethylsiloxy)-5-methylnon-1-yne in Example 1(1), there was obtained (3R,4R)-2-methylene-3-[(3'S,5,'RS)-3'-(t-butyldimethylsiloxy)-5',9'-dimethyldec-8'-en-1'-ynyl]-4-(t-butyldimethylsiloxy)cyclopentan-1-one.

$^1$H-NMR(CDCl$_3$, 300MHz) δ ppm:
0.10 and 0.13(2s, 12H), 0.80~1.02(m, 21H), 1.05~1.82(m, 5H), 1.60(s, 3H), 1.67(s, 3H), 1.90~2.06(m, 2H), 2.33(dd, J=7.4Hz, 17.8Hz, 1H), 2.33(dd, J=7.4Hz, 17.8Hz, 1H), 2.71(dd, J=6.4Hz, 17.8Hz, 1H), 3.49~3.57(m, 1H), 4.22~4.37(m, 1H), 4.45(t, J=5.9Hz, 1H), 5.08(t, J=6.1Hz, 1H), 5.55(d, J=1.8Hz, 1H), 6.14(d, J=2.5Hz, 1H)

(2) Following similar manners to those of Examples 1(2) (3) using the compound obtained in the above item (1), the title compound was obtained.

$^1$H-NMR(CDCl$_3$, 300MHz) δ ppm:
0.95(d, J=6.4Hz, 3H), 1.13~1.86(m, 15H), 1.60(s, 3H), 1.68(s, 3H), 1.92~2.07(m, 2H), 2.17~2.35(m, 2H), 2.30(t, J=7.5Hz, 2H), 2.60~2.68(m, 1H), 2.75(dd, J=7.1Hz, 18.4Hz, 1H), 3.66(s, 3H), 4.28~4.37(m, 1H), 4.42~4.53(m, 1H), 5.09(t, J=6.2Hz, 1H)

IR (neat):
3380, 2920, 2220, 1750, 1430, 1160, 1070, 830, 720cm$^{-1}$

EXAMPLE 3

(17R)-17 20-Dimethyl-13 14-didehydro-PGE$_1$ methyl ester (Compound 2)

(1) Following a substantially similar manner to that of Example 1(1) but using (3S,5R)-3-(t-butyldimethylsiloxy)-5-methylnon-1-yne in place of (3S,5S)-3-(t-butyldimethylsiloxy)-5-methylnon-1-yne in Example 1(1), there was obtained (3R,4R)-2-methylene-3-[(3,'S,5'R)-3'-(t-butyldimethylsiloxy)-5'-methylnon-1'-ynyl]-4-(t-butyldimethylsiloxy)cyclopentan-1-one.

$^1$H-NMR (CDCl$_3$, 300MHz) δ ppm:
0.03~0.15(m, 12H), 0.80~0.93(m, 24H), 1.06~1.80(m, 9H), 2.33(dd, J=7.4Hz, 17.9Hz, 1H), 2.71(dd, J=6.4Hz, 17.9Hz, 1H), 3.41~3.56(m, 1H), 4.20~4.32(m, 1H), 4.44(t, J=6.59Hz, 1H), 5.55(br. s, 1H), 6.14(br. s, 1H)

IR(neat):
2920, 2850, 2210, 1730, 1630, 1450, 1360, 1240, 1100, 1080, 820, 760cm$^{-1}$ (2) Following similar manners to those of Examples 1(2) and (3) using the compound obtained in the above item (1), the title compound was obtained.

$^1$H-NMR (CDCl$_3$, 300MHz) δ ppm:
0.80~0.98(m, 6H), 1.08~1.86(m, 19H), 2.16~2.35(m, 2H), 2.31(t, J=7.4Hz, 2H), 2.55~2.81(m, 1H), 2.74(dd, J=7.0Hz, 18.2Hz, 1H), 3.67(s, 3H), 4.26~4.53(m, 2H)

IR(neat): 3390, 2930, 2860, 2240, 1740, 1460, 1260, 1170, 1070, 730cm$^{-1}$

EXAMPLE 4

(17S)-17,20-Dimethyl-13,14-didehydro-PGE$_1$ (Compound 3)

To a solution of the compound (290 mg, 0.735 mmol) obtained in Example 1 in 14.5 ml of 50% (v/v) acetone—water were added 130.5 ml of phosphate butter solution (10 mM, pH 7.0) and then 500 μl (242 units) of pig liver esterase, followed by stirring at room temperature. The reaction was traced by thin-layer chromatography, after confirming the disappearance of the material (about 15 hours), the reaction mixture was extracted with ethyl acetate, washed with a saturated aqueous sodium chloride solution, dried and concentrated. The resulting crude product was purified by silica gel column chromatography (eluent; ethyl acetate: methanol=40:1) to give 115 mg of the title compound.

$^1$H-NMR(CDCl$_3$, 300MHz) δ ppm:
0.80~1.00(m, 6H), 1.05~1.90(m, 19H), 2.15~2,32(m, 2H), 2.30(t, J=7.4Hz, 2H), 2.62(dd, J=8.4Hz, 11.3Hz, 1H), 2.73(dd, J=7.2Hz, 18.4Hz, 1H), 4.25~4.35(m, 1H), 4.45(dt, J=1.5Hz, 7.1Hz, 1H)

IR (neat):
3392, 2931, 2859, 2238, 1740, 1713, 1463, 1411, 1380, 1235, 1162, 1077, 758cm$^{-1}$ EXAMPLES 5 and 6

The compounds prepared in the following Examples 5 and 6 are those obtained by following a similar hydrolysis to that of Example 4 using compounds obtained in Examples 2 and 3, respectively.

EXAMPLE 5

(17RS)-20-Nor-17-methyl-19-(2'-methylprop-1'-enyl-13,14-didehydro-PGE$_1$ (Compound 4)

$^1$H-NMR(CDCl$_3$, 300MHz) δ ppm:

0.94(d, J=6.3Hz, 3H), 1.10∼1.81(m, 15H), 1.60(s, 3H), 1.68(s, 3H), 1.90∼2.04(m,2H), 2.18∼2.29 (m, 1H), 2.23(dd, J=9.3Hz, 18.4Hz, 1H), 2.34(t, J=7.2Hz, 2H), 2.60∼2.69(m, 1H), 2.75(dd, J=7.1Hz, 18.4Hz, 1H), 4.27∼4.36(m, 1H), 4.48(t, J=6.2Hz, 1H), 5.09(t, J=6.3Hz, 1H)

IR(neat):

3350, 2920, 2330, 1710, 1440, 1380, 1260, 1160, 1070, 830, 720cm$^{-1}$

EXAMPLE 6

(17R)-17 20-Dimethyl-13 14-didehydro-PGE$_1$ (Compound 5)

$^1$H-NMR(CDCl$_3$, 300MHz) δ ppm:

0.85∼0.97 (m, 3H), 0.93(d, J=6.6Hz, 1.10∼1.84(m, 19H), 2.17∼2.30(m, 1H), 2.24(dd, J=9.2Hz, 18.5Hz, 1H), 2.35(t, J=7.3Hz, 2H), 2.65(ddd, J=1.7Hz, 8.3Hz, 11.4Hz, 1H), 2.76(ddd, J=1.2Hz, 7.3Hz, 18.5Hz, 1H), 4.27∼4.37(m, 1H), 4.43∼4.52(m, 1H)

IR(neat):

3369, 2930, 2859, 2237, 1740, 1713, 1462, 1384, 1235, 1159, 1071cm$^{-1}$

EXAMPLE 7

(17R)- 17,20-Dimethyl-13,14-didehydro-PGE$_1$ (Compound 5)

(1) A solution of copper (I) cyanide.dilithium dichloride (2.16 g, 12.4 mmol) in tetrahydrofuran (12.4 ml) was added at −70° C. to 5-carbo[(prop-2'-enyl)oxy]-pentylzinc (II) iodide (0.62M tetrahydrofuran solution, 16.0 ml, 9.92 mmol), followed by stirring at the same temperature for 15 minutes. To the solution were added at −70° C., (3R,4R)-2-methylene-3-[(3'S,5'R)-3'-(t-butyldimethylsiloxy)-5'-methylnon-1'-ynyl]-4-(t-butyl-dimethylsiloxy)cyclopentan-1-one (2.44 g, 4.95 mmol) obtained in Example 3(1) and a solution of trimethylsilyl chloride (1.13 ml, 8.91 mmol) in diethyl ether, followed by stirring to raise the temperature to room temperature over about a 2 hour period. The reaction solution, after addition of a saturated aqueous ammonium chloride solution (80 ml), was extracted with n-hexane. The organic layer was washed with a saturated aqueous sodium chloride solution, dried and concentrated. The resulting residue was dissolved in ether—isopropyl alcohol (1:4, 25 ml) and then pyridinium p-toluenesulfonate (62 mg, 0.25 mmol) was added thereto, followed by stirring at room temperature for 12 hours. After addition of ether (30 ml) and a saturated aqueous sodium bicarbonate solution (10 ml), the reaction solution was extracted, and the organic layer was dried and concentrated. The resulting residue was chromatographed on silica gel column (n-hexane: ether =4:1) to give 2.57 g of (17R)-17,20-dimethyl-13,14-didehydro-PGE$_1$ allyl ester 11,15-bis(t-butyldimethylsilyl ether).

$^1$H-NMR(CDCl$_3$, 300MHz) δ ppm:

0.09(s, 6H), 0.11(S, 3H), 0.13(s, 3H), 0.82∼0.95(m, 6H), 0.89(s, 18H), 1.06∼1.82(m, 19H), 2.14∼2.26(m, 1H), 2.16(dd, J=6.8Hz, 18.2Hz, 1H), 2.32(t, J=7.5Hz, 2H), 2.59∼2.75(m, 2H), 4.22∼4.35(m, 1H), 4.36∼4.48(m, 1H), 4.57(ddt, J=1.4Hz, 1.4Hz, 5.7Hz, 2H), 5.23 (ddt, J=1.4Hz, 1.4Hz, 10.3Hz, 1H), 5.31(ddt, J=1.4Hz, 1.4Hz, 17.2Hz, 1H), 5.92(ddt, J=5.7Hz, 10.3Hz, 17.2Hz, 1H)

IR(neat):

2955, 2930, 2858, 2234, 1747, 1650, 1463, 1383, 1253, 1162, 1093cm$^{-1}$ (2) Tetrakis(triphenylphosphine)pallasium(0) (32.4 mg, 0.028 mmol) was added to a solution of the compound (182 mg, 0.280 mmol) obtained in the above item (1) in tetrahydrofuran (2.8 ml), followed by stirring at room temperature for 10 minutes. To this was added morpholine (0.130 ml, 1.49 mmol), followed by stirring at room temperature for 20 minutes. After addition of a saturated aqueous sodium chloride solution (10 ml), the mixture was extracted with n-hexane (40 ml), and the organic layer was dried and concentrated. The resulting residue was chromatographed on silica gel column (n-hexane: ether=9:1) to give 130 mg of (17R)-17,20-dimethyl-13,14-didehydro-PGE$_1$ 11,15-bis(t-butyldimethylsilyl ether).

$^1$H-NMR(CDCl$_3$, 300MHz) δ ppm:

0.09(s, 3H), 0.10(s, 3H), 0.11(s, 3H), 0.13(s, 3H), 0.82∼0.94(m, 24H), 1.05∼1.80(m, 19H), 2.11∼2.25(m, 1H), 2.16(dd, J=7.0Hz, 18.2Hz, 1H), 2.34(t, J=7.5Hz, 2H), 2.62∼2.73(m, 1H), 2.66(ddd, J=1.2Hz, 6.6Hz, 18.2Hz, 1H), 4.24∼4.33(m, 1H), 4.38∼4.45(m, 1H)

IR(neat):

2931, 2858, 2237, 1748, 1713, 1464, 1380, 1253, 1122, 1092cm$^{-1}$ (3) A 50% aqueous hydrofluoric acid solution (9.1 ml) was added at 0° C. to a solution of the compound (688 mg, 1.13 mmol) obtained in the above item (2) in acetonitrile (38 ml), followed by stirring at 0° C. for 90 minutes. The reaction solution was poured into ethyl acetate (50 ml)—a saturated aqueous sodium bicarbonate solution (300 ml), extracted with ethyl acetate, washed with a saturated aqueous sodium chloride solution, dried and concentrated. The resulting residue was purified by silica gel column chromatography (ether: ethyl acetate=1:1) to give 365 mg of the title compound (identical to the compound of Example 6).

EXAMPLE 8

17R)-17,20-Dimethyl-13 14-didehydro-PGE$_1$ allyl ester (1) Following a substantially similar manner to that of Example 1(3) using the compound obtained in Example 7(1), the title compound was obtained.

$^1$H-NMR(CDCl$_3$, 300MHz) δ ppm:

0.84∼0.98(m, 3H), 0.93(d, J=6.6Hz, 3H), 1.08∼1.84(m, 19H), 2.16(d, J=5.2Hz, 1H), 2.19∼2.29(m, 1H), 2.23(dd, J=9.2Hz, 18.5Hz, 1H), 2.33(dd, J=7.5Hz, 2H), 2.64(ddd, J=1.7Hz, 8.3Hz, 11.3Hz, 1H), 2.71(d, J=3.6Hz, 1H), 2.75(ddd, J=1.3Hz, 7.2Hz, 18.5Hz, 1H), 4.27∼4.38(m, 1H), 4.42∼4.52(m, 1H), 4.57(ddd, J=1.4Hz, 1.4Hz, 5.7Hz, 2H), 5.23(ddt, J=1.4Hz, 1.4Hz, 10.4Hz, 1H), 5.31 (ddt, J=1.4Hz, 1.4Hz, 17.2Hz, 1H), 5.92(ddt, J=5.7Hz, 10.4Hz, 17.2Hz, 1H)

IR(neat):

3412, 2931, 2859, 2235, 1741, 1650, 1461, 1382, 1236, 1163, 1073, 990, 933, 771cm$^{-1}$

We claim:

1. A prostaglandin E$_l$ analogue represented by the formula:

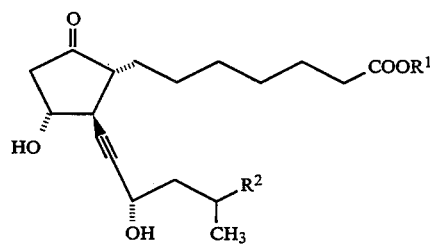

(wherein $R^1$ is a hydrogen atom, an alkyl group having 1 to 6 carbon atoms or an allyl group, and $R^2$ is an alkyl group having 3 to 6 carbon atoms or an alkenyl group having 3 to 6 carbon atoms), or a salt thereof.

2. A compound represented by the formula:

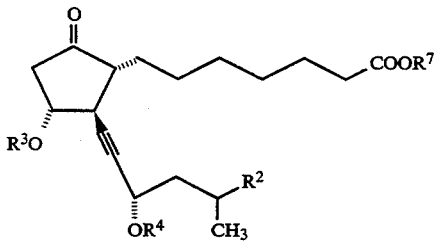

(wherein $R^7$ is an alkyl group having 1 to 6 carbon atoms or an allyl group, and $R^2$ is an alkyl group having 3 to 6 carbon atoms or an alkenyl group having 3 to 6 carbon atoms, $R^3$ and $R^4$ are the same or different, and are each a hydroxyl protecting group).

3. A $PGE_1$ analogue in accordance with claim 1 wherein $R^1$ is an alkyl group having 1–6 carbon atoms.

4. A $PGE_1$ analogue in accordance with to claim 1 wherein $R^2$ is an alkyl group having 3–6 carbon atoms.

5. A $PGE_1$ analogue in accordance with claim 2 wherein $R^2$ is an alkyl group having 3–6 carbon atoms.

6. 17,20-dimethyl-13,14-didehydro-$PGE_1$, methyl ester.

7. A $PGE_1$ analogue in accordance with claim 1 wherein $R^1$ is a hydrogen atom.

8. 17,20-dimethyl-13,14-didehydro-$PGE_1$.

9. 17,20-dimethyl-13,14-didehydro-$PGE_1$ ethyl ester.

* * * * *

UNITED STATES PATENT AND TRADEMARK OFFICE
CERTIFICATE OF CORRECTION

PATENT NO. : 5,449,815           Page 1 of 2
DATED      : September 12, 1995
INVENTOR(S): SATO et al It is certified that error appears in the above-indentified patent and that said Letters Patent is hereby corrected as shown below:

On title page, item [75] Inventors:

"Takehiro Amano, Urawa; Kazuya Kameo, Kounosu; Tohru Tanami, Tokyo; Masaru Mutoh, Ohmiya; Naoya Ono, Tokyo; Jun Goto, Ohmiya"

should read:

--Takehiro Amano, Saitama; Kazuya Kameo, Saitama; Tohru Tanami, Tokyo; Masaru Mutoh, Saitama; Naoya Ono, Tokyo; Jun Goto, Saitama--.

Col. 7, line 44, delete "%".

Col. 8, line 15, "17S" should read --(17S)--.

Col. 9, line 13, delete "6" insert --δ--;
         line 47, "17RS)" should read --(17RS)--; and
         line 66, after "1(2)" insert --and--.

UNITED STATES PATENT AND TRADEMARK OFFICE
CERTIFICATE OF CORRECTION

PATENT NO. : 5,449,815
DATED : September 12, 1995
INVENTOR(S) : SATO et al

It is certified that error appears in the above-indentified patent and that said Letters Patent is hereby corrected as shown below:

Col. 10, line 10, after "17" insert a comma --,--.

Col. 11, line 14, after "17" insert a comma --,--;
          line 17, after "6.6Hz" insert --3H)--.

Col. 12, line 36, "17R)" should read --(17R)- and after "13" insert a comma --,--.

Signed and Sealed this

Eighteenth Day of June, 1996

Attest:

BRUCE LEHMAN

Attesting Officer          Commissioner of Patents and Trademarks